United States Patent [19]
Vanmaele et al.

[11] Patent Number: 5,888,750
[45] Date of Patent: Mar. 30, 1999

[54] METHOD OF RECOVERING SHIGA-LIKE TOXINS AND VACCINES COMPRISING INACTIVATED SHIGA-LIKE TOXIN

[75] Inventors: Rosa Vanmaele; Glen D. Armstrong, both of Edmonton, Canada

[73] Assignee: Synsorb Biotech, Inc., Calgary, Canada

[21] Appl. No.: 866,921

[22] Filed: May 30, 1997

[51] Int. Cl.$^6$ .................................................. G01N 33/53
[52] U.S. Cl. ...................... 435/7.8; 435/7.37; 436/527; 436/541; 536/53; 536/124; 530/413; 424/241.1
[58] Field of Search .................... 424/241.1; 436/541, 436/527; 435/7.8, 7.37; 536/53, 124; 530/413

[56] References Cited

U.S. PATENT DOCUMENTS

| | | |
|---|---|---|
| 4,137,401 | 1/1979 | Lemieux et al. . |
| 4,238,473 | 12/1980 | Lemieux et al. . |
| 4,362,720 | 12/1982 | Lemieux et al. . |
| 4,738,926 | 4/1988 | Hamada et al. ......................... 435/239 |
| 5,168,049 | 12/1992 | Meade et al. ........................... 435/69.1 |
| 5,620,858 | 4/1997 | Armstrong et al. . |

OTHER PUBLICATIONS

Voet et al. *Biochemistry,* 2d Edition, 1995 pp. 85–88.
Acheson et al., *One step High Yield Affinity Purification of Shiga–Like Toxin II Variants and Quantitation using Enzyme Linked Immunosorbent Assays,* Microb. Pathog. 14:57–66 (1993).
Acheson et al., *Expression and Purification of Shiga–Like Toxin II B Subunits,* Infect. Immun. 63:301–308 (1995).
Acheson et al., *Enzyme–Linked Immunosorbent Assay for Shiga Toxin and Shiga–like Toxin II Using P1 Glycoprotein from Hydatid Cysts,* J. Infect. Dis. 161:134–137 (1990).
Alkout et al., *Isolation of a Cell Surface Component of Helicobacter pylori That Binds H Type 2, Lewis$^a$, and Lewis$^b$ Antigens,* Gastroent. 112:1179–1187 (1997).
Amvam–Zollo, P., et al., *Streptococcus pneumoniae Type XIV Polysaccharide: Synthesis of a Repeating Branched Tetrasaccharide with Dioxa–Type Spacer–Arms,* Carbohydrate Research, 150:199–212 (1986).
Armstrong et al., *Investigation of Shiga–like Toxin Binding to Chemically Synthesized Oligosaccharide Sequences,* J. Infect. Dis. 164:1160–1167 (1991).
Boulanger et al., *Universal Method for the Facile Production of Glycolipid/Lipid Matrices for the Affinity Purification of Binding Ligands,* Analytical Biochem. 217:1–6 (1994).
Brown et al., *Digalactosyl–Containing Glycolipids as Cell Surface Receptors for Shiga Toxin of Shigella dysenteriae 1 and Related Cytotoxins of Escherichia coli,* Rev. Infec. Dis. 13(Suppl 4):S298–303 (1991).
Calderwood et al., *A System for Production and Rapid Purification of Large Amounts of the Shiga Toxin/Shiga–Like Toxin I B Subunit,* Infect. Immun. 58:2977–2982 (1990).

Chernyak, A. Y., et al., *A New Type of Carbohydrate–Containing Synthetic Antigen: Synthesis of Carbohydrate–Containing Polyacrylamide Copolymers having the Specificity of 0:3 and 0:4 Factors of Salmonella,* Carbohydrate Research, 128:269–282 (1984).
Dahmén, J., et al., *Synthesis of space arm, lipid, and ethyl glycosides of the trisaacharide portion [αD–Gal–(1–4)–β–D–Gal(1–4)–β–D–Glc] of the blood group p$^k$ antigen: preparation of neoglycoproteins,* Carbohydrate Research, 127: 15–25 (1984).
Dahmén, J., et al., *2–Bromoethyl glycosides: applications in the synthesis of spacer–arm glycosides,* Carbohydrate Research, 118: 292–301 (1983).
Donohue–Rolfe et al., *Purification of Shiga Toxin and Shiga–Like Toxins I and II by Receptor Analog Affinity Chromatography with Immobilized P1 Glycoprotein and Production of Cross–Reactive Monoclonal Antibodies,* Infect. Immun. 57:3888–3893 (1989).
Donohue–Rolfe et al., *Shiga Toxin: Purification, Structure, and Function,* Rev. Infect. Dis. 13 (Suppl 4:):S293–7 (1991).
Ekborg, G., et al., *Synthesis of Three Disaccharides for the Preparation of Immunogens bearing Immunodeterminants Known to Occur on Glycoproteins,* Carbohydrate Research, 110: 55–67 (1982).
Fernandez–Santana, V., et al., *Glycosides of Monoallyl Diethylene Glycol. A New type of Spacer group for Synthetic Oligosaccharides,* J. Carbohydrate Chemistry, 8(3):531–537 (1989).
Garegg, P.J., et al., *A Synthesis of 8–Methoxycarbonyloctyl–1–yl O–α–D–Galactopyranosyl–(1–3)–0–β–D–Galactopyranosyl–(1–4)–2–Acetamido–2–Deoxy–β–D–Glucopyranoside,* Carbohy. Res., 136: 207–213 (1985).
Lee, R. T., et al., *Synthesis of 3–(2–Aminoethylthio)PropylGlycosides,* Carbohydrate Research, 37:193–201 (1974).
Lemieux, R.U., et al., *The properties of a 'synthetic' antigen related to the blood–group Lewis A,* J. Am. Chem. Soc., 97:4076–83 (1975).
O'Brien et al., *Purification of Shigella Dysenteriae 1 (Shiga)–Like Toxin From Escherichia coli O157:H7 Strain Associated with Haemorrhagic Colitis,* Lancet Sep. 3, 1983, p. 573.
Paulsen, H., *Synthese von oligosaccharid–determinanten mit amid–spacer vom typ des T–antigens,* Carbohydr. Res., 104:195–219 (1982).

(List continued on next page.)

*Primary Examiner*—James C. Housel
*Assistant Examiner*—Jennifer Shaver
*Attorney, Agent, or Firm*—Burns, Doane, Swecker & Mathis, L.L.P.

[57] ABSTRACT

Disclosed are methods of purifying shiga-like toxins (SLTs) from Polymyxin B sulfate extracts of Verotoxin-producing *Escherichia coli*. The methods are facile, efficient and reproducible. In another aspect, the toxin is inactivated for use in a vaccine against SLT mediated disease conditions.

6 Claims, 1 Drawing Sheet

OTHER PUBLICATIONS

Pozsgay et al., *Purification of Subunit B of Shiga Toxin Using a Synthetic Trisaccharide–Based Affinity Matrix*, Bioconj. Chem. 7:45–55 (1996).

Rana, S. S., et al., *Synthesis of Phenyl 2–Acetamido–2–Deoxy–3–O–α–L–Fucopyranosyl–β–D–Glucopyranoside and Related Compounds*, Carbohydrate Research, 91:149–157 (1981).

Rappuoli, R., *Toxin Inactivation and Antigen Stabilization: Two Different Uses of Formaldehyde*, Vaccine, 12:579–581 (1994).

Ryd et al., *Purification of Shiga toxin by α–D–galactose–(1–4)–β–D–galactose–(1–4)–β–D–glucose–(1)receptor ligand–based chromatography*, FEBS Letters 258:320–322 (1989).

Waddell et al., *Induction of Verotoxin Sensitivity in Receptor–Deficient Cell Lines Using the Receptor Glycolipid Globotriosylceramide*, Proc. Natl. Acad. Sci. 87:7898–7901 (1990).

METHOD OF RECOVERING SHIGA-LIKE TOXINS AND VACCINES COMPRISING INACTIVATED SHIGA-LIKE TOXIN

BACKGROUND OF THE INVENTION

Field of the Invention

This invention, in one aspect, is directed to methods for recovering Shiga-like toxins (SLT) from a sample under physiologically acceptable conditions using an affinity ligand covalently attached to a solid support. The use of such a covalently attached affinity ligand enhances the purity of the product and these methods employ mildly basic conditions to effect elution of the SLT from the affinity support thereby avoiding the use of acidic conditions and, in particular, harsh acidic conditions.

In another aspect, the SLTs recovered in this invention are inactivated to provide for an immunoprotective vaccine.

References

The following references and patents are cited in this application as superscript numbers:

1. Boulanger et al., Universal Method for the Facile Production of Glycolipid/Lipid Matrices for the Affinity Purification of Binding Ligands, Analytical Biochem. 217:1–6 (1994).
2. Armstrong et al., Investigation of Shiga-like Toxin Binding to Chemicaly Synthesized Oligosaccharide Sequences, J. Infect. Dis. 164:1160–1167 (1991).
3. Pozsgay et al., Purification of Subunit B of Shiga Toxin Using a Synthetic Trisaccharide-Based Affinity Matrix, Bioconj. Chem. 7:45–55 (1996).
4. Donohue-Rolfe et al., Purification of Shiga Toxin and Shiga-Like Toxins I and II by Receptor Analog Affinity Chromatography with Immobilized P1 Glycoprotein and Production of Cross-Reactive Monoclonal Antibodies, Infect. Immun. 57:3888–3893 (1989).
5. Brown et al., Digalactosyl-Containing Glycolipids as Cell Surface Receptors for Shiga Toxin of Shigella dysenteriae 1 and Related Cytotoxins of Escherichia coli, Rev. Infect. Dis. 13(Suppl 4):S298–303 (1991).
6. Ryd et al., Purification of Shiga toxin by α-D-galactose-(1-4 )-β-D-galactose-(1-4)-β-D-glucose-(1-) receptor ligand-based chromatography, FEBS Letters 2:320–322 (1989).
7. Acheson et al., One step High Yield Affinity Purification of Shiga-Like Toxin II Variants and Quantitation using Enyme Linked Immunosorbent Assays, Microb. Pathog. 14:57–66 (1993).
8. Donohue-Rolfe et al., Shiga Toxin: Purification, Structure, and Function, Rev. Infect. Dis. 13(Suppl 4):S293–7 (1991).
9. Waddell et al., Induction of Verotoxin Sensitivity in Receptor-Deficient Cell Lines Using the Receptor Glycolipid Globotriosylceramide, Proc. Natl. Acad. Sci. 87:7898–7901 (1990).
10. Acheson et al., Expression and Purification of Shiga-Like Toxin II B Subunits, Infect. Immun. 63:301–308 (1995).
11. O'Brien et al., Purification of Shigella Dysenteriae 1 (Shiga)-Like Toxin From *Escherichia coli* 0157:H7 Strain Associated with Haemorrhagic Colitis, Lancet Sep. 3, 1983, page 573.
12. Calderwood et al., A System for Production and Rapid Purification of Large Amounts of the Shiga Toxin/ Shiga-Like Toxin I B Subunit, Infect. Immun. 58:2977–2982 (1990).
13. Acheson et al., Enzyme-Linked Immunosorbent Assay for Shiga Toxin and Shiga-like Toxin II Using P1 Glycoprotein from Hydatid Cysts, J. Infect. Dis. 161:134–137 (1990).
14. Armstrong, et al., Method of Removing Shiga-Like Toxins From Biological Samples, U.S. Pat. No. 5,620,858, issued Apr. 17, 1997
15. Rafter, et al., U.S. patent application Ser. No. 08/669,004, filed Jun. 21, 1996, TREATMENT OF BACTERIAL DYSENTERY
16. Lemieux, R. U., et al., The properties of a 'synthetic' antigen related to the blood-group Lewis A, J. Am. Chem. Soc., 97:4076–83 (1975).
17. Ekborg, G., et al., Synthesis of Three Disaccharides for the Preparation of Immunogens bearing Immunodeterminants Known to Occur on Glycoproteins, Carbohydrate Research, 110: 55–67 (1982).
18. Dahmén, J., et al., 2-Bromoethyl glycosides: applications in the synthesis of spacer-arm glycosides, Carbohydrate Research, 118: 292–301 (1983).
19. Rana, S. S., et al., Synthesis of Phenyl 2-Acetamido-2-Deoxy-3-O-α-L-Fucopyranosyl-β-D-Glucopyranoside and Related Compounds, Carbohydrate Research, 91:149–157 (1981).
20. Amvam-Zollo, P., et al., Streptococcus pneumoniae Type XIV Polysaccharide: Synthesis of a Repeating Branched Tetrasaccharide with Dioxa-Type Spacer-Arms, Carbohydrate Research, 150:199–212 (1986).
21. Paulsen, H., Synthese von oligosaccharid-determinanten mit amid-spacer vom typ des T-antigens, Carbohydr. Res., 104:195–219 (1982).
22. Chernyak, A. Y., et al., A New Type of Carbohydrate-Containing Synthetic Antigen: Synthesis of Carbohydrate-Containing Polyacrylamide Copolymers having the Specificity of 0:3 and 0:4 Factors of Salmonella, Carbohydrate Research, 128:269–282 (1984).
23. Fernandez-Santana, V., et al., Gtycosides of Monoaltyl Diethylene GlycoL A New type of Spacer group for Synthetic Oligosaccharides, J. Carbohydrate Chemistry, 8(3):531–537 (1989).
24. Lee, R. T., et al., Synthesis of 3-(2-Aminoethylthio) PropylGlycosides, Carbohydrate Research, 37:193–201 (1974).
25. Lemieux, R. U., et al., Gtycoside-Ether-Ester Compounds, U.S. Pat. No. 4,137,401, issued Jan. 30, 1979.
26. Lemieux, R. U., et al., Artificial Oligosaccharide Antigenic Determinants, U.S. Pat. No. 4,238,473, issued Dec. 9, 1980.
27. Lemieux, R. U., et al., Synthesis of 2-Amino-2-Deoxyglycoses and 2-Amino-2-Deoxyglycosides from glycals, U.S. Pat. No. 4,362,720, issued Dec. 7, 1982.
28. Dahmén, J., et al., Synthesis of space arm, lipid, and ethyl glycosides of the trisaccharide portion [α-D-Gal-(1-4)-β-D-Gal(1-4)-β-D-Glc] of the blood group p$^k$ antigen: preparation of neoglycoproteins, Carbohydrate Research, 127: 15–25 (1984).
29. Garegg, P. J., et al., A Synthesis of 8-Methoxycarbonyloctyl-1-yl O-α-D-Galactopyranosyl-(1-3)-0-β-D-Galactopyranosyl-(1-4) -2-Acetamido-2-Deoxy-β-D-Glucopyranoside, Carbohy. Res., 136: 207–213 (1985).

30 Rappuoli, R., Toxin Inactivation and Antigen Stabilization: Two Different Uses of Formaldehyde, Vaccine, 12:579–581 (1994)

All of the above references are herein incorporated by reference in their entirety to the same extent as if each individual reference was specifically and individually indicated to be incorporated herein by reference in its entirety.

State of the Art

*Shigella dysenteriae* type 1, is the Shigella serotype responsible for the most severe cases of bacillary dysentery. This bacteria produces a protein, Shiga toxin, that possesses potent neurotoxic, cytotoxic and enterotoxic effects which are well understood in the art and is the causative agent in shigellosis.

*Escherichia coil* is an indigenous member of the intestinal tract of humans and animals where it facilitates digestion. Enterovirulent *E. coli* organisms, however, differ from the normal *E. coil* residents of the intestinal tract because of their ability to invade the intestinal mucosa and to produce enterotoxins. Certain pathogenic strains of *E. coil* elaborate a toxin that is cytotoxic for African green monkey (Vero) cells. Hence, the term "Verotoxin" was introduced to describe this cytotoxic activity.

Verotoxins from different *E. coli* strains constitute a family of structurally and functionally related cytotoxins, the prototype of which is Shiga toxin. Thus, the term Shiga-like toxin (SLT) is synonymous with Verotoxin. Shiga-like toxins are proteins secreted by certain pathogenic strains of *E. coli* and are the causative agents of numerous disease conditions such as hemorrhagic colitis, hemolytic uremic syndrome and the like.

Different antigenically distinct SLTs have been described including SLT-I and SLT-II. SLT-I is nearly identical to Shiga toxin. SLT-II, including known variants of SLT-II, is related but is not neutraled by anti-Shiga toxin serum. Both toxins are comprised of multiple copies of a B subunit and a single A subunit. The B subunit is approximately 7.5 kDa and is associated with receptor binding. The A subunit is approximately 35 kDa and is responsible for the catalytic inhibition of protein synthesis. SLT-I and SLT-II are 60% homologous overall and 70% homologous in the B subunit.

SLT-producing *E. coli* belong to several different serotypes but all have in common the ability to secrete one or more SLTs. In North America, the 0157:H7 *E. coli* serotype is isolated from 95% of cases of SLT mediated infections whereas, in other locations, different enterohemrrhagic *E. coil* serotypes predominate. Serotype 0157:H7 *E. coli* can readily be identified in the clinical laboratory because of its inability to utilize sorbitol as a carbon source. However, clinical laboratories that rely only on sorbitol fermentation to test for SLT mediated infections will fail to identify such infections arising from non-0157:H7 *E. coli* serotypes. This, of course, is a major concern in those regions where non-0157:H7 serotypes predominate. Accordingly, clinical diagnosis of SLT mediated infections in a patient by assaying only for the presence of enterohemoffhagic 0157:H7 *E. coli* serotypes is not advised.

Another diagnostic method is the detection of SLTs in the stools of patients suspected of being infected with enterohemorrhagic *E. coli*. Diagnostic kits used in the detection of SLTs are now commercially available but, nevertheless, these tests require a purified source of SLT, preferably SLT I and SLT II, to serve as a positive control. Moreover, with increased recognition of this disease condition the need for and usage of these diagnostic kits will continue to increase.

Thus, a facile, efficient method of recovering SLTs from a sample would be desirable.

In addition to diagnostic utility, methods for providing large quantities of purified SLTs are also required for use in prophylactic treatment regimens for patients, particularly patients with weakened immune systems, wherein inactivated forms of the SLTs could be used as an immunoprotective vaccine.

Specifically, enterohemorrhagic *E. coli* infections are treated clinically as self-limiting because antibiotics are of little therapeutic value. The failure of antibiotic therapy may relate to the central role of SLT in the disease, and antibiotics are not directed at reducing the activity of these toxins. Accordingly, alternative methods of therapeutically treating SLT mediated infections, including hemolytic uremic syndrome (HUS), have been proposed including the oral ingestion of an affinity ligand to the SLT which ligand is covalently attached to a solid inert support through a non-peptidyl linker arm.[14] In such treatment, the affinity ligand complexes with the toxin in vivo and is subsequently eliminated as part of the patient's stool thereby lowering toxin levels in the infected individual.

In such treatment regimens, it has been reported, however, that the incidence of HUS is reduced by the administration of this affinity ligand during a critical period after onset of the disease.[15] While such time critical treatment regimens would, of course, reduce the incidence of HUS, the difficulty in diagnosis of the SLT mediated disease conditions coupled with the possibility that the infected individual would not present himself/herself to a physician during this critical time period, suggests that prophylactic methods to prevent enterohemorrhagic *E. coli* infection are desirable, particularly in individuals susceptible to such infections.

As it relates to this last aspect, it is a fundamental that a major defense mechanism of humans and animals against infection by pathogenic organisms, such as SLT-producing *E. coli*, is their ability to produce antibodies that bind to the pathogens and their toxins, inactivating them or preparing them for destruction by specialized cells in the body. In the very young, i.e., infants, an undeveloped immune system may not provide adequate protection against such infections. In elderly patients, an incompetent immune system may likewise fail to provide protection. Accordingly, any person with a compromised immune system could suffer a lethal infection upon first exposure to enterohemorrhagic *E. coli*-infection if their immune system was not primed. One method for so priming such persons would be to administer an immunoprotective vaccine to that person which vaccine would prophylactically act to prevent the occurrence of this disease.

Such vaccines would, of course, require purification of SLTs which are subsequently inactivated. Various methods have been heretofore disclosed for isolating SLTs. These methods, however, are in one manner or another not preferred for preparing large quantities of purified SLTs for use in a vaccine. For example, receptor analog affinity chromatography with a glycoprotein present in hydatid cyst fluid has been utilized.[4,7,10,13] This glycoprotein possesses a trisaccharide, $\alpha Gal(1\rightarrow 4)\beta Gal(1\rightarrow 4)GlcNAc$, that is identical to the erythrocyte P1 glycolipid. However, safety concerns regarding possible contamination of the isolated SLTs would preclude the use of these recovered SLTs in vaccine preparations.

The glycolipid $Gb_3$ ($\alpha Gal(1\rightarrow 4)\beta Gal(1\rightarrow 4)\beta Glc$-ceramide) has also been used to bind and remove SLTs from a sample. In Boulanger[1], the $Gb_3$ was adsorbed noncovalently onto Celite. The lack of a covalent linkage between the glycolipid and the affinity support would, in principle, allow the glycolipid to leach from the affinity support. Upon elution of the SLTs one cannot ensure that some of the glycolipid has leached from the affinity support into the SLT. Thus, contamination of the SLTs by small amounts of Gb3 is possible and such contamination would preclude its use in the preparation of a vaccine.

Others have used glycoconjugates or glycolipids containing the disaccharide sequence αGal(1→4)βGal covalently linked to a solid support to bind the SLTs. Subsequent elution from these substrates has required harsh and/or denaturing conditions. For example, guanidine HCl[3,6], 10% SDS in boiling water[2], MgCl$_2$[4,7,8,10,12] all have been used. The protein thus recovered may lose antigenic epitopes, be less immunogenic and, consequently, provide an inferior vaccine.

From the above it is apparent that a need for a rapid, inexpensive method of recovering shiga-like toxins is desirable. Further, a safe, immunoprotective vaccine is desirable.

SUMMARY OF THE INVENTION

This invention provides a facile, efficient and reproducible method for recovering biologically active Shiga-like toxins from a sample using an affinity ligand covalently attached to an affinity support. The method is based on specific elution conditions required to recover the biologically active Shiga-like toxins from the affinity support thereby avoiding the problems associated with the prior art. The affinity ligand is covalently bound to the support obviating concerns that the ligand may leach from the solid support. Further, the methods do not utilize any glycoconjugate to effect recovery of the SLT eliminating possible contamination and safety concerns in the preparation of the vaccine.

Accordingly, in one of its method aspects, this invention is directed to a method for recovering shiga-like toxins (SLT) from a sample comprising said toxins which method comprises:
  i) contacting said sample with an affinity support having an affinity ligand comprising the disaccharide subunit αGal(1→4)βGal covalently linked to the affinity support through a compatible linker arm to form a SLT-affinity support complex;
  ii) separating the SLT-affinity support complex from the sample;
  iii) recovering free SLT from the complex under basic non-denaturing conditions;
     wherein the purified SLT is essentially free of glycolipids.

In another of its method aspects, this invention is directed to a method for recovering shiga-like toxin I (SLT-I) from a sample comprising said toxins which method comprises:
  i) contacting said sample with an inert solid affinity support having a disaccharide subunit αGal(1→4)βGal covalently linked to the affinity support through a non-peptidyl compatible linker arm to form a SLT-I/affinity support complex;
  ii) separating the SLT-I/affinity support complex from the sample;
  iii) recovering free SLT-I from the complex by contacting the complex with an aqueous solution having a pH of from about 8 to 11 to provide SLT-I in the aqueous solution and the affinity support;
  iv) separating the aqueous solution from the affinity support.

In still another of its method aspects, this invention is directed to a method for recovering shiga-like toxin II (SLT-II) from a sample comprising said toxins which method comprises:
  i) contacting said sample with an affinity support having an affinity ligand comprising the disaccharide subunit αGal(1→4)βGal covalently linked to the affinity support through a non-peptidyl compatible linker arm to form a SLT-II/affinity support complex;
  ii) separating the SLT-II/affinity support complex from the sample;
  iii) recovering free SLT-II from the complex by contacting the complex with an aqueous basic solution of urea having a urea molarity of from about 0.5 to 3M to provide SLT-II in the aqueous solution and the affinity support;
  iv) separating the aqueous solution from the affinity support.

In a composition aspect, this invention is directed to inactivated SLTs which are useful as vaccines. Accordingly, in this aspect, this invention is directed to an immunoprotective vaccine against SLT mediated disease conditions which vaccine comprises an immunoprotective amount of inactivated SLT and a pharmaceutically acceptable carrier.

DETAILED DESCRIPTION OF THE INVENTION

Figure 1:
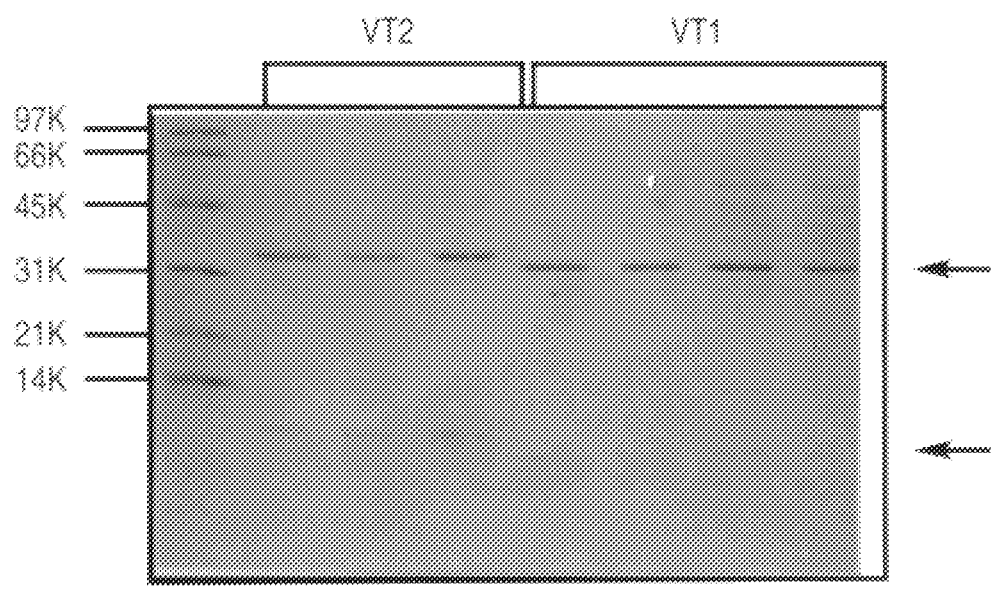
FIG. 1 shows an SDS-PAGE analysis of several SLT-I and SLT-II preparations. The SLT-I and SLT-II A and B subunit bands are indicated by arrows. The molecular weights (×10$^3$) of the pre-stained standards used to calibrate the gels are shown on the left side of the figure.

This invention is directed to a facile, efficient and reproducible method for recovering biologically active Shiga-like toxins. The methods of the invention take advantage of the binding specificities of the various SLTs. The methods employ mildly basic, non-denaturing conditions during the elution recovery step. The methods provide an economical supply of SLTs for use, e.g., in the preparation of an immunoprotective vaccine.

Definitions

Before discussing the methodology of the present invention, the following terms will be defined.

The term "shiga-like toxins" or "SLT" as used herein refers to a group of toxins produced by enterohemorrhagic *E. coli* that resemble the Shigella-produced shiga toxins as commonly understood in the art. Such SLTs include Shiga-like toxin I and Shiga-like toxin II (SLT-II) and variants thereof, as recognized in the art, that recognize host cell globo series glycolipid receptors containing αGal(1→4)βGal (galabiose) in the nonreducing terminal position of their oligosaccharide sequences.

All of the SLT's are multimeric proteins composed of an enzymatic (A) subunit and multiple (B) subunits. The B oligomer is the binding portion of the toxin that allows it to bind to host cell receptors. The A subunit has an enzymatic activity (N-glycosidase) that depurinates 28S ribosomal RNA in mammalian cells. This enzymatic activity abolishes the ability of the toxin-infected cell to perform protein synthesis.

Rapid tight binding of SLTs to P$_1$ disaccharide [αGal(1→4)βGal], P$_1$ trisaccharide [αGal(1→4)βGal(1→4)

βGlcNAc], or $P_k$ trisaccharide [αGal(1→4)βGal(1→4)βGlc] is demonstrated by the Verocytotoxicity neutralization assays.

The term "sample" as used herein means an aqueous or organic solution comprising SLTs such as, for example, growth media from the culture of enterohemorrhagic *E. coli* and the like.

The term "basic" as used herein means a pH of greater than 7. Preferably the pH is in the range of about 8 to 11. More preferably the pH is in the range of about 8.5 to 10.

"Immunogenic" means capable of eliciting an immune response. An immunogenic epitope means that portion of a molecule which is recognized by the immune system to cause production of antibodies. Preferably the response is immunoprotective.

"Protectively immunogenic" or "immunoprotective" means stimulating a T cell dependent (TD) immune response. Such a response is characterized by the ability to elicit significant levels of IgG and opsonic activity. An immunological memory is developed to the immunogenic antigen such that the antibodies produced ameliorate the infection and disease condition mediated by the pathogen.

The term "inactivated SLT" means the detoxified SLT. A detoxified or inactivated SLT is substantially free of biologic activity while retaining a high degree of immunogenicity. The inactivated toxin fails to produce the local or systemic effects of SLTs when administered to a human or animal but elicits an immunoprotective response such that upon subsequent challenge with an active SLT the human or animal is unaffected. The inactivated toxin is suitable for use in a vaccine directed against SLT mediated disease conditions. Alternatively, the inactivated toxin may serve as a carrier protein for weakly immunogenic antigens.

"Hapten" means an antigen, including an incomplete or partial antigen which may not be capable, alone, of causing the production of antibodies. A hapten may elicit a T cell independent immune response.

The term "biocompatible" refers to chemical inertness with respect to animal or human tissues or body fluids. Biocompatible materials are non-sensitizing.

The term "compatible linker arm" refers to a moiety which serves to space the oligosaccharide structure from the biocompatible solid support and which is bifunctional wherein one functional group is capable of binding to a reciprocal functional group of the support and the other functional group is capable of binding to a reciprocal functional group of the oligosaccharide structure. Compatible linker arms preferred in the present invention are non-peptidyl linker arms. That is to say that the linker arms do not employ a peptide group to link the oligosaccharide structure to the solid support.

The term "affinity support" refers to an inert, solid material to which the oligosaccharide sequences are bound via a compatible linker arm.

Methodology

The bacterial strains used were *E. coli* JM101 (pJB128) (F traD 36 lacγDM15 proA$^+$ proB$^+$ lacI$^q$/lac pro supE thi) and C600 (933W). The JM101 strain contained the SLT-I operon isolated from the genome of *E. coli* H-19B cloned into pTZ18-R. The C600 strain contained the SLT-II sequences from bacteriophage 933W.

Synthesis of Affinity Support

The compositions useful in the methods of this invention include oligosaccharides comprising an αGal(1→4)βGal disaccharide subunit covalently linked via a compatible linker arm to a solid, inert support. Preferably the compatible linker arm is non-peptidyl. In one preferred embodiment, the oligosaccharide is the disaccharide αGal (1→4)βGal. In another preferred embodiment, the oligosaccharide is a trisaccharide with the disaccharide αGal(1→4) βGal preferably in the non-reducing terminus of the oligosaccharide. In a preferred embodiment the trisaccharide is αGal(1→4)βGal(1→4)βGlc.

The chemical synthesis of the SYNSORB-$P_1$ AND SYNSORB-$P_k$ (8-methoxycarbonyloctyl (MCO)-glycosides coupled to CHROMOSORB-P) has been described previously.[16] Further, U.S. patent application Ser. No. 08/781,327 entitled as "PROCESSES FOR THE PREPARATION OF αGal(1→4)βGal(1→4)Glc-OR" filed on Jan. 10, 1997 as Attorney Docket No. 026579-045 which application is incorporated herein by reference in its entirety discloses methods for synthesis of αGal(1→4)βGal(1→4)Glc-OR trisaccharides.

In general, the chemical synthesis of all or part of the oligosaccharide glycosides first involves formation of a glycosidic linkage on the anomeric carbon atom of the reducing sugar of a mono- or disaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

The affinity supports to which the oligosaccharide structures of the present invention are bound through the aglycon may be in the form of particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Solid supports made of inorganic materials are preferred. Preferably the solid supports have a particle size of from about 10 to 500 microns. In particular, particle sizes of 100 to 200 microns are preferred.

The term "SYNSORB" refers to synthetic 8-methoxycarbonyloctyl oligosaccharide structures covalently coupled to CHROMOSORB P™ (Manville Corp., Denver, Colo.)[6], which is a derivatized silica particle.

Synthetic oligosaccharide sequences covalently attached to a biocompatible solid support, e.g., CHROMOSORB P™ (SYNSORB), are used to bind SLT toxins or Verotoxins. These compositions are useful to recover SLTs from a sample and are particularly preferred because they are non-toxic and resistant to mechanical and chemical deposition. SYNSORBs have been found to possess a high density of oligosaccharide moieties which is particularly useful for binding SLT.

For purposes of this application, all sugars are referenced using conventional three letter nomenclature. All sugars are assumed to be in the D-form unless otherwise noted. Further all sugars are in the pyranose form.

Linking moieties that are used in indirect bonding are preferably organic bifunctional molecules of appropriate length (at least one carbon atom) which serve to distance the oligosaccharide structure from the surface of the solid support.

The compositions of this invention are preferably represented by the formula:

(X-Y-R)$_n$-SOLID SUPPORT where X comprises an oligosaccharide having a terminal non-reducing αGal(1→4)βGal group and which contains at least two 2 sugar units and preferably no more than 6 sugar units which oligosaccharide binds to the shiga-like toxin, Y is oxygen, sulfur or nitrogen, R is an aglycon linking arm of at least 1 carbon atom, SOLID SUPPORT is as defined above, and n is an integer greater than or equal to 1. Preferred aglycons are from 1 to about 20 carbon atoms. Oligosaccharide sequences containing about 1 to 10 saccharide units may be used. Sequences with 2 to 3 saccharide units are preferred. Preferably, n is an integer such that the composition contains about 0.25 to 2.50 micromoles oligosaccharide per gram of composition.

Numerous aglycon linking arms are known in the art. For example, a linking arm comprising a para-nitrophenyl group (i.e., —OC$_6$H$_4$pNO$_2$) has been disclosed.[17] At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed.[18] Specifically, the linking arm is derived from a 2-bromoethyl group which, in a substitution reaction with thionucleophiles, has been shown to lead to linking arms possessing a variety of terminal functional groups such as —OCH$_2$CH$_2$SCH$_2$CO$_2$CH$_3$ and —OCH$_2$CH$_2$SC$_6$H$_4$-pNH$_2$. These terminal functional groups permit reaction to complementary functional groups on the solid support, thereby forming a covalent linkage to the solid support. Such reactions are well known in the art.

A 6-trifluoroacetamido-hexyl linking arm (—O—(CH$_2$)$_6$-NHCOCF$_3$) has been disclosed[19] in which the trifluoro-acetamido protecting group can be removed, unmasking the primary amino group used for coupling.

Other exemplifications of known linking arms include the 7-methoxycarbonyl-3,6,dioxaheptyl linking arm[20] (—OCH$_2$—CH$_2$)$_2$OCH$_2$CO$_2$CH$_3$); the 2-(4-methoxycarbonyl-butancarboxamido)ethyl[21] (—OCH$_2$CH$_2$NHC(O)(CH$_2$)$_4$CO$_2$CH$_3$); the allyl linking arm[22] (—OCH$_2$CH=CH$_2$) which, by radical co-polymerization with an appropriate monomer, leads to co-polymers; other allyl linking arms[23] are known (—O (CH$_2$CH$_2$O)$_2$CH$_2$CH=CH$_2$). Additionally, allyl linking arms can be derivatized in the presence of 2-aminoethanethiol[24] to provide for a linking arm —OCH$_2$CH$_2$CH$_2$SCH$_2$CH$_2$NH$_2$. Other suitable linking arms have also been disclosed[25-29].

Preferably, the aglycon linking arm is a hydrophobic group and most preferably, the aglycon linking arm is a hydrophobic group selected from the group consisting of —(CH$_2$)$_8$C(O)—, —(CH$_2$)$_5$OCH$_2$CH$_2$CH$_2$— and —(CH$_2$)$_8$CH$_2$O—. Non-peptidyl linking arms are preferred for use as the compatible linking arms of the present invention.

The compositions useful in the conduct of the methods of the invention comprise the αGal(1→4)βGal disaccharide subunit which subunit can be used alone or in conjunction with a higher oligosaccharide, e.g., the αGal(1→4)βGal (1→4)βGlcNAc trisaccharide or αGal(1→4)βGal(1→4) βGlc trisaccharide. The αGal(1→4)βGal disaccharide subunit is preferably found at the non-reducing terminus of an oligosaccharide.

The oligosaccharide is coupled to a solid support or coupled directly, preferably through a linking arm such as that described by Lemieux et al.[16]. The di and trisaccharide units may also be coupled directly to pharmaceutically acceptable carriers or constitute a portion of an oligosaccharide coupled to such carriers.

Disaccharide (SYNSORB-P) Purification of Shiga-Like Toxins

It has been surprisingly found that while SLT-I cannot be eluted from the trisaccharide affinity support disclosed herein under basic non-denaturing conditions it can be recovered from the disaccharide affinity support under the same conditions.

The SLTs are isolated by disrupting the bacterial cell membrane to release the periplasmic contents including the toxin into the liquid sample. Such methods are known in the art and include treatment with polymyxin B, sonication and the like. Preferably the cells are incubated with polymyxin B.

The toxin is separated from cellular debris by any method known in the art such as filtration, extraction, centrifugation and the like. Preferably the liquid sample is centrifuged at a sufficient speed and for an appropriate time to pellet cellular debris. The supernatant or fraction containing the toxin is used in the next step.

The affinity support with the affinity ligand attached thereto is brought into contact with the toxin containing liquid sample. The affinity support may be added directly to the liquid sample under agitation. Alternatively, an affinity support column may be prepared and the liquid sample passed therethrough. Regardless of the mode of contact, the affinity support and liquid sample are brought into contact preferably at a temperature ranging from about 0° C. to about 80° C. for a time sufficient to allow the toxin and the affinity support to form a complex. A particularly preferred temperature range is from about 25° C. to about 40° C. Depending on the temperature, the contact time is preferably from about 1 to 60 minutes and more preferably the contact time ranges from about 3 to 30 minutes.

The complexes are then preferably washed several times with a buffer solution to remove contaminants. Appropriate buffer solutions are, for example, phosphate buffered saline (PBS), Tris buffered saline (TBS), and the like. Preferably, the wash buffer has a pH of between 2.5 and 7.5. In a preferred embodiment the wash buffer is acidic with a pH of between about 3 and about 5.

The bound toxin is eluted from the complex using an elution solution having a basic pH such that will not denature the toxin. It has been advantageously found that there is no requirement for a high salt concentration in such solutions. Thus, for example, a suitable solution (e.g., Tris buffered aqueous solutions) with a pH of between 8 and 11 may be utilized. In a preferred embodiment the pH range will be from about 8.5 to about 10.

Removal of endotoxin is done by any method known in the art such as, for example, passage over an appropriate affinity gel. Preferably, the levels of endotoxin do not exceed 0.01 ng/mL.

The toxin thus recovered may be stored in the refrigerator at 4° C. Alternatively, the recovered toxin may be proportioned and frozen at about −70° C. Additionally, the recovered toxin may be lyophilized to form a powder for pharmaceutical use in, for example, a vaccine.

Trisaccharide (SYNSORB-Pk) Puification of Shiga-Like Toxins

It has been surprisingly found that under the basic non-denaturing conditions utilized for the recovery of SLTs from the disaccharide affinity support, SLT-I cannot be eluted from the trisaccharide affinity support. Thus, use of the trisaccharide can advantageously be used to selectively recover SLT-II. It is understood, however, that if recovery of both SLT-I and SLT-II is desired, then the disaccharide structure should be employed, In any event, the method of recovery of SLT-II is as described for SLT-I preferably, however, with the following modifications.

Preferably, the cells are pre-incubated with Mitomycin C for a time sufficient to induce lytic growth of the lysogenic bacteriophage prior to release of the periplasmic contents. The elution buffer additionally comprises urea in a concentration ranging from about 1M to about 5M. The pH is adjusted as necessary to a pH range of about 8.0 to about 11.0, preferably from about 8.5 to about 10. Under these basic non-denaturing conditions SLT-I remains substantially bound to the affinity support while the SLT-II is recovered.

Biological activity of the recovered SLTs was determined using the Vero cytotoxicity assay as previously described.[2]

Inactivation of SLTs

The recovered toxins, prepared as above, are suitable for use in an immunoprotective vaccine once they have been inactivated. The toxins may be inactivated by any means known in the art. Such methods include treatment with formaldehyde, exposure to alkali metal salts of oxymethane sulfinic acid, protease treatment in the presence of sulfhydryl reducing agents and the like. See *Vaccine Preparation Techniques*, edited by J. I. Duffy, 1980. A preferred method is formaldehyde treatment of the toxin.

The biologically active toxin is contacted with an effective amount of the deactivating agent chosen such that the toxin retains immunogenic epitopes but lacks toxicity. The deactivation techniques to arrive at immunoprotective vaccines are well within the skill of the art and, include variations in, for example, the concentration of the deactivating agent, the contact time, the temperature of treatment, etc. A skilled practitioner would be able to modify the conditions of detoxification to obtain optimum results. Detoxification may be verified using the Vero cytotoxicity test as previously described.[2]

Preferably, the detoxified SLT is then dialyzed against a physiologic saline solution to remove the deactivating agent and filtered through a suitable sterilizing filter, thus providing sterile, detoxified SLT useful as a fluid vaccine. The fluid vaccine may be lyophilized to form a powder useful in the formulation of a pharmaceutical composition. Such pharmaceutical compositions may be tablets, powders, sterile aqueous solutions and the like.

An adjuvant may optionally be added to the thus obtained fluid or solid vaccine. An adjuvant is any substance whose admixture with the detoxified SLT increases the immunological response. Such adjuvants are well known in the art and include, for example, surface-active agents (e.g., saponins and Quil-A), aluminum hydroxide or phosphate, oil-water emulsions, muramyl dipeptide derivatives and the like.

The SLT vaccine may be administered intraperitoneally, intramuscularly, orally and the like. For oral administration, the fluid vaccine is preferably given with an appropriate antacid buffer to protect against digestion in the stomach. Alternatively, the sterile, detoxified SLT may also be encapsulated into biodegradable microparticles, entrapped in liposomes, conjugated to a protein with lectin or lectin-like binding activity to glycoproteins or glycolipids in the intestinal mucosa or co-administered as an immunostimulating complex and the like for vaccine administration.

Biodegradable microparticles for either oral or parenteral use (including intramuscularly) are prepared from polymers approved by the FDA for parenteral use in humans. These polymers have a well established record of safety and biocompatibility. The prepared microparticles are taken up by the Peyer's patches of the gut-associated lymph tissue, then phagocytosed by macrophages. Oral vaccine administration advantageously induces both secretory and systemic immunoprotection.

The detoxified toxin may be used in a vaccine directed to enterohemorrhagic *E. coli* SLTs and associated disease conditions. Alternatively, the inactivated toxin may be used as a carrier protein for haptens and T-cell independent antigens. Such a carrier protein simulates an immunoprotective response to a hapten and converts a T-cell independent antigen into a T-cell dependent antigen.

The dosage of the vaccine necessary is readily determined by the attending clinician in view of the weight, age, physical condition and the like of the individual to be treated.

Preferably, the detoxified SLT, with or without an adjuvant, is admixed with a pharmaceutically acceptable carrier for administration. In making the pharmaceutical compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is mined to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyfrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the active agent is employed at no more than about 20 weight percent of the pharmaceutical composition, more preferably no more than about 15 weight percent, with the balance being pharmaceutically inert carrier(s).

The tablets or pills of the present invention may be coated or otherwise compounded to provide a dosage form affording the advantage of prolonged action. For example, the tablet or pin can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

In order to further illustrate the present invention and advantages thereof, the following specific examples are given, it being understood that the same are intended only as illustrative and not in any way limiting.

EXAMPLES

In these examples and elsewhere, the following abbreviations have the following meanings. If not defined, any abbreviation used in this application has its generally accepted meaning.

° C.=degrees Celsius
L=liter
M=molar
mg=milligrams
mL=milliliter
mM=millimolar
ng=nanograms
nm=nanometers
rpm=rotations per minute
SDS=sodium dodecyl sulfate
TSB=tryptic soy broth
$\mu$g=microgram
$\mu$L=microliter Example 1

Recovery of SLTs

E. coli JM101 (pJLB128) was grown in 1 L TSB supplemented with 50 $\mu$g/mL carbenicillin in 2.8 L triple baffled Fembach flasks. The flasks were inoculated with 100 mL of a stationary phase overnight culture.

Cultures were incubated at 37° C. on a New Brunswick Scientific model G10 high capacity shaker table oscillating at 115 rpm. Bacterial growth was monitored spectrophotometrically ($\lambda$600 nm) and when the cultures reached mid to late log phase, Polymyxin B sulfate was added to a final concentration of 0.1 mg/mL. The cultures were incubated for an additional 30 minutes and then centrifuged at 3500× g at 4° C. to sediment bacterial cell debris. Next, SYNSORB-P1 disaccharide (15 gram/L) was added to the cell-free culture supernatant solution and the resulting mixture was incubated, with vigorous shaking, for 30 minutes at room temperature. is The SYNSORB-P1 disaccharide was then collected by filtration and washed with 250 mM NaCl (pH 3.8). The absorbance of the NaCl washes was monitored at $\lambda$280 nm. When the absorbance of the wash fractions returned to baseline value, bound SLT-I was eluted from the SYNSORB-P1 using 50 mM Tris base (pH 10) containing 250 mM NaCl. The solution was then concentrated using an Amicon ultrafiltration unit fitted with a YM 10 (10,000 molecular weight cutoff) filter. Concentrated SLT-I solution was stored in the refrigerator at 4° C. or samples were frozen at −70° C. or −20° C.

SLT-II was purified from E. coli strain C600 following essentially the same procedure described above for SLT-I. The only modifications to the SLT-II preparation were that the SYNSORB-Pk trisaccharide was substituted for SYNSORB-P1 disaccharide and, the mid- to late-log phase cultures were incubated with 250 ng/mL Mitomycin C for 6 hours, to induce lytic growth of the lysogenic bacteriophage, prior to treatment with Polymyxin B sulfate. Also, 1M urea was added to the Tris-base, pH 10.0, 250 mM NaCl SLT-II elution buffer.

Example 2

P1 Trisaccharide Results

The purpose of this example is to illustrate that SLT-I binds so tightly to SYNSORB Pk trisaccharide that SLT-I cannot be eluted therefrom. Specifically, SLT-I was bound to SYNSORB Pk trisaccharide in the manner described in Example 1 above. Then, the following elution conditions were employed to effect recovery of SLT-I from the SLT-I/SYNSORB Pk trisaccharide complex:

1. 50 mM Tris (pH 10), 250 mM NaCl;
2. 50 mM Tris (pH 10), 250 mM NaCl, 1M urea;
3. 4.5M $MgCl_2$, 20 minute incubation time; and
4. 4.5M $MgCl_2$, 72 hour incubation time.

Due to tight binding, SLT-I was not recovered from the SLT-I/SYNSORB complex using any of these conditions.

Example 3

Analysis of Recovered SLT

The amount of SLT activity eluted from the SYNSORB-P1 disaccharide in Example 1 was determined in the Vero cytotoxicity assay. The amount of SLT activity present in Polymyxin-treated, late log phase cultures incubated without SYNSORB-P1 disaccharide was also determined and the percent recovery of SLT-I from SYNSORB-P1 was computed using these data (Table 1). In ten independent experiments, the recovery of SLT-I activity from the Polymyxin extracted cultures averaged 61% (SD mean 8, range 48% to 76%).

TABLE 1

Summary of SLT Preparations

| SLT Type | Protein conc. (mg/mL)[a] | Frac. SLT[b] | mL conc. prep. | Total mg SLT[c] | No. of Liters Processed | % Recovery[d] | Yield (mg/L)[e] |
|---|---|---|---|---|---|---|---|
| SLT I  | 0.47 | 0.38  | 3.5 | 0.63  | 5  | 59   | 0.13 |
| SLT I  | 0.55 | 0.40  | 2.5 | 0.55  | 5  | 64   | 0.11 |
| SLT I  | 0.64 | 0.89  | 3.5 | 1.99  | 5  | 59   | 0.40 |
| SLT I  | 0.90 | 0.31  | 3.5 | 0.98  | 5  | 53   | 0.20 |
| SLT I  | 1.17 | 0.94  | 3.5 | 3.85  | 5  | 48   | 0.77 |
| SLT I  | 0.80 | 0.11  | 3.5 | 0.31  | 5  | 59   | 0.06 |
| SLT I  | 0.85 | —     | 4.5 | —     | 10 | 70   | —    |
| SLT I  | 0.86 | 0.81  | 4.5 | 3.14  | 10 | 64   | 0.31 |
| SLT I  | 2.74 | —     | 5.0 | —     | 10 | 76   | —    |
| SLT I  | 2.22 | 0.64  | 5.0 | 7.10  | 10 | 61   | 0.71 |
| SLT II | 1.17 | N.D.[f] | 7.5 | 8.80 | 5 | N. D. | 1.76 |
| SLT II | 2.69 | N.D.  | 4.5 | 12.12 | 5  | N. D. | 2.42 |
| SLT II | 0.97 | N.D.  | 6.0 | 5.84  | 5  | N. D. | 1.17 |

[a]Determined using the Pierce BCA procedure.
[b]Purity calculated using the formula [(CD$_{50}$ × 4.4 pg/mL × 10)/Protein conc].
[c]Protein conc. × Frac. SLT-I × mL conc. prep.
[d]Calculated as described in Example 2.
[e]Total mg SLT-I/Liters processed.
[f]N. D. Not yet determined.

SDS-PAGE analysis of SLT-I and SLT-II eluted from SYNSORB-P

SDS-PAGE analysis of SLT-I and SLT-II eluted from the SYNSORB revealed two prominent bands (FIG. 1). The gels were stained with Coomassie blue. The SLT-I and SLT-II A and B subunit bands are indicated by arrows on the right side of the figure. The molecular weights (×10$^3$) of the pre-stained standards used to calibrate the gels are shown on the left side of the figure. Each lane contained 2.4 μg protein/18 μL diluted 1:1 with SDS sample buffer. The molecular weight of the upper bands was calculated to be 31,500 (SLT-I) and 34,300 (SLT-II) relative to the protein standards. The lower bands were very broad and spanned the range from 6 KDa to 11 KDa. A sharper band was often observed at the trailing (upper) edge of these broad lower bands. The average molecular weight at the center of the broad bands was estimated to be 7,700. Minor stained bands were also detected in some of these preparations (last two lanes on the right hand side of FIG. 1). SDS-PAGE analysis of SLT preparations confirmed the stability of these preparations during storage.

Amino terminal microsequence analysis

Ten amino terminal microsequencing cycles were performed on the upper bands and 8 cycles were performed on the lower bands, including the sharper trailing band in the SDS polyacrylamide gels. The microsequence data from the upper bands matched the Genebank sequences for the SLT-I and SLT-II A subunits at all ten positions. Similarly, the microsequence data from the broad, lower bands unambiguously confirmed their identity as the SLT-I and SLT-II B subunits.

Removal of endotoxin from the SLT preparations

The SLT-I and SLT-II preparations eluted from the SYNSORB contained significant amounts of endotoxin, average of 7 ng/mL, determined by the colorimetric Limulus Amebocyte Lysate (LAL) assay. The level of endotoxin in the SLT preparations was reduced to less than 0.01 ng/mL by a single passage through Detoxi-Gel endotoxin removing gel from Pierce.

The yield of purified SLT-I was approximately 0.4 mg/L of culture (Table 1) and its specific activity in the Vero cytotoxicity assay was 4.4 pg/mL/CD$_{50}$ (a solution containing SLT at a concentration of 4.4 pg/mL was cytotoxic to 50% of the Vero cells in a monolayer).

The bro ad appeaance of the 6 KDa to 11 KDa SLT B subunit bands on SDS-polyacrylamide gels is typical of these toxins. Others[1] have previously reported this observation. The results of microsequence analysis of these B subunit bands indicated the presence of only one amino terminal group. Therefore, it is unlikely the broad appearance of this band resulted from protein degradation during purification since this would have resulted in the appearance of multiple amino terminal groups.

The unambiguous amino terminal sequence data from the broad, 6 KDa to 11 KDa bands, suggests that the sharper band at their trailing edges is not a contaminant because this would have contributed an additional signal to the amino terminal sequence analysis. However, we cannot discount the possibility that the sharper, trailing edge band may have had a modified amino terminal group that rendered it resistant to microsequencing. Nonetheless, the reactivity of this sharper band with anti-SLT-I, PH1, monoclonal antibodies in western immunoblots (data not shown) support the idea that this is not a contaminant of the preparations and perhaps represents an artifact of the SDS-PAGE procedure.

The SYNSORB-purified SLT preparations maintained their biological activity during several months of frozen (−70° C.) storage or storage at 4° C. in the refrigerator.

Example 4

Vaccine Preparation

The recovered SLT from Example 1 are inactivated by contacting with formol, an aqueous solution of formaldehyde. The toxin is incubated with 0.035–0.7% formol at a temperature of about 37° C. for a period of between 1 to 6 weeks. The end of the reaction is determined by the Vero cytotoxicity test.

The inactivated toxin is dialyzed against phosphate buffered saline (PBS) and sterile filtered to yield a fluid preparation useful as a vaccine.

While the invention has been described in terms of various preferred embodiments, the skilled artisan will appreciate that various modifications, substitutions, omissions and changes may be made without departing from the scope thereof. Accordingly, it is intended that the scope of the present invention be limited solely by the scope of the following claims, including equivalents thereof.

What is claimed is:

1. A method for recovering shiga-like toxins (SLI) from a sample containing said toxins which method comprises:
   i) contacting said sample with an affinity support having an affinity ligand comprising the disaccharide subunit αGal(1→4)βGal covalently linked to the affinity support through a compatible linker arm to form a SLT-affinity support complex;
   ii) separating the SLT-affinity support complex from the sample;
   iii) recovering free SLT from the complex under basic non-denaturing conditions;
   wherein the purified SLT is essentially free of glycolipids.

2. A method for recovering shiga-like toxin I (SLT-I) from a sample containing said toxins which method comprises:
   i) contacting said sample with an inert solid affinity support having a disaccharide subunit αGal(1→4)βGal covalently linked to the affinity support through a non-peptidyl compatible linker arm to form a SLT-affinity support complex;
   ii) separating the SLT-affinity support complex from the sample;
   iii) recovering free SLT-I from the complex by contacting the complex with an aqueous solution having a pH of from about 8 to 11 to provide SLT-I in the aqueous solution and the affinity support;
   iv) separating the aqueous solution from the affinity support.

3. The method of claim 2 wherein the pH of the aqueous solution in part iii) is from about 8.5 to 10.5.

4. A method for recovering shiga-like toxin II (SLT-II) from a sample containing said toxins which method comprises:
   i) contacting said sample with an affinity support having an affinity ligand comprising the disaccharide subunit αGal(1→4)βGal covalently linked to the affinity support through a non-peptidyl compatible linker arm to form a SLT-affinity support complex;
   ii) separating the SLT-affinity support complex from the sample;
   iii) recovering free SLT-II from the complex by contacting the complex with an aqueous basic solution of urea having a urea molarity of from about 0.5 to 3M to provide SLT-II in the aqueous solution and the affinity support;
   iv) separating the aqueous solution from the affinity support.

5. The method according to claim 4 wherein the molarity of the urea is from 1 to 3M.

6. The method according to claim 4 wherein said affinity ligand is αGal(1→4)βGal(1→4)Glc.

* * * * *